US006036925A

United States Patent [19]

Adams et al.

[11] Patent Number: 6,036,925

[45] Date of Patent: Mar. 14, 2000

[54] AIR FRESHENER TAPER CANDLE PRODUCT

[75] Inventors: Mary Beth Adams, County of Lake, Ill.; Judith R. Zaunbrecher, Village of Wind Point; Luz P. Requejo, Racine, both of Wis.

[73] Assignee: S. C. Johnson & Son, Inc., Racine, Wis.

[21] Appl. No.: 08/992,389

[22] Filed: Dec. 17, 1997

[51] Int. Cl.[7] .................................. A61L 9/01; C10L 5/00

[52] U.S. Cl. .......................... 422/126; 422/305; 431/288; 44/275

[58] Field of Search .................................... 422/126, 305; 431/288; 44/275

[56] References Cited

U.S. PATENT DOCUMENTS

| | | |
|---|---|---|
| 1,974,037 | 9/1934 | Atkins . |
| 2,090,297 | 8/1937 | Knoche . |
| 2,379,250 | 6/1945 | Muskat et al. . |
| 2,415,040 | 1/1947 | Rust . |
| 2,818,615 | 1/1958 | Burness . |
| 2,829,511 | 4/1958 | Oesterle et al. . |
| 3,065,502 | 11/1962 | Lorenian . |
| 3,175,876 | 3/1965 | Fredericks . |
| 3,332,428 | 7/1967 | Mold et al. . |
| 3,351,695 | 11/1967 | Hollingsworth . |
| 3,499,452 | 3/1970 | Kallianos et al. . |
| 3,560,122 | 2/1971 | Cassar . |
| 3,577,588 | 5/1971 | Chisholm . |
| 3,630,697 | 12/1971 | Duling et al. . |
| 3,705,890 | 12/1972 | Barker et al. . |
| 3,898,039 | 8/1975 | Lin . |
| 3,940,233 | 2/1976 | Fox et al. . |
| 4,092,988 | 6/1978 | Van Auken et al. . |
| 4,134,714 | 1/1979 | Driskill . |
| 4,155,979 | 5/1979 | Powell . |
| 4,278,658 | 7/1981 | Hooper et al. . |
| 4,302,409 | 11/1981 | Miller et al. . |
| 4,449,987 | 5/1984 | Lindauer . |
| 4,507,077 | 3/1985 | Sapper . |
| 4,568,270 | 2/1986 | Marcus et al. . |
| 4,663,315 | 5/1987 | Hasegawa et al. . |
| 4,708,851 | 11/1987 | Von Loringhoven . |
| 5,068,321 | 11/1991 | Buysch et al. . |
| 5,069,231 | 12/1991 | Rutherford . |
| 5,081,104 | 1/1992 | Orson, Sr. . |
| 5,313,002 | 5/1994 | De Heij et al. . |
| 5,320,798 | 6/1994 | Chambon et al. . |
| 5,538,018 | 7/1996 | Chan et al. . |
| 5,569,799 | 10/1996 | Chen et al. . |
| 5,645,845 | 7/1997 | Neumann et al. . |

FOREIGN PATENT DOCUMENTS

| | | |
|---|---|---|
| 56-011995 | 2/1981 | Japan . |
| 9-188893 | 1/1998 | Japan . |
| WO97 09072 | 9/1996 | WIPO . |
| WO99 08722 | 2/1999 | WIPO . |

*Primary Examiner*—Elizabeth McKane

[57] ABSTRACT

This invention provides an air freshener candle product which is a slender combustible body composed of ingredients which include (1) candle-wax, (2) thermoplastic polymer and (3) particulate air freshener-release filler. The air freshener is released into the atmosphere under candle burning conditions. An invention taper-shaped candle can be produced by a continuous molding process.

20 Claims, No Drawings

AIR FRESHENER TAPER CANDLE PRODUCT

CROSS-REFERENCE TO RELATED PATENT APPLICATION

The subject matter of this patent application is related to that disclosed in patent application Ser. No. 08/992,000, filed Dec. 17, 1997.

BACKGROUND OF THE INVENTION

This invention generally relates to the dispensing of an air freshener from a candle product. More specifically this invention relates to a wickless candle having a content of air freshener ingredient which is released under candle combustion conditions.

Candles have been known and used since early civilization. A typical candle is formed of a solid or semi-solid body of wax such as paraffin wax, stearic acid, or beeswax, and it contains an axially embedded combustible fibrous wick.

When the wick of a candle is lit, the generated heat melts the solid wax, and the resulting liquid flows up the wick by capillary action and is combusted.

More recently candles have been developed that appeal to the olfactory as well as the visual sense. This type of candle usually incorporates a fragrance oil in the wax body. As the wax is melted in a lighted candle, there is a release of the fragrance oil from the liquified wax pool.

Conventional fragrance candles have drawbacks because of cost and other considerations. The incorporation of fragrance oil in candlewax is difficult to achieve in a quantity which ensures the release of a suitable level of fragrance into the atmosphere during candle burning. Further, the incorporated fragrance tends to migrate and volatilize from the wax body prematurely. The fragrance also softens the wax body, and there is an undesirable loss of rigidity in the candle structure.

There is continuing interest in the development of improved fragrance and other types of air freshener candle products.

Accordingly, it is an object of this invention to provide an air freshener candle product which releases air freshener into the atmosphere only under the pyrolysis conditions of the burning candle.

It is another object of this invention to provide a taper-shaped wickless air freshener candle product.

It is a further object of this invention to provide an air freshener candle product which can be produced by a continuous molding process.

Other objects and advantages of the present invention shall become apparent from the accompanying description and examples.

Publications of background interest relative to the present invention include U.S. Pat. Nos. 2,379,250; 2,829,511; 3,332,428; 3,560,122; 3,499,452; 3,705,890; 3,898,039; 4,092,988; 4,568,270; 5,538,018; and 5,569,779; incorporated by reference.

U.S. Pat. No. 2,829,511 describes a candle wick structure composed of a core strand of cellulose acetate in combination with an outer web of cotton fibers.

U.S. Pat. No. 3,560,122 describes a wick composition which is composed of paraffin wax, polyethylene and particulate palygorskite clay.

U.S. Pat. No. 5,538,018 describes a flavorant-release additive which is a cellulose derivative that is incorporated into a cigarette paper wrapper.

DESCRIPTION OF THE INVENTION

One or more objects of the present invention are accomplished by the provision of an air freshener candle product which is a taper-shaped combustible body comprising:

(a) between about 45–85 weight percent of candlewax ingredient;

(b) between about 10–35 weight percent of thermoplastic polymer ingredient; and (c) between about 0.1–20 weight percent of particulate air freshener-release cellulosic filler ingredient;

wherein the air freshener constituent is released into the atmosphere under candle burning conditions.

The term "taper-shaped" as employed herein refers to a slender candle body which can be rigid, semi-rigid or flexible, and which can be circular, square, rectangular oval, hexagonal, or any other geometric shape for esthetic appeal. A typical cylindrical candle body can have a diameter between about 0.3–1.5 centimeters.

The candlewax ingredient can be selected from commercially available wax media. The combustible body of a candle product typically is a thermoplastic blend of organic materials such as beeswax, paraffin wax, montan wax, carnauba wax, microcrystalline wax, fatty alcohols, fatty acids, fatty esters, and the like.

The polymer ingredient of an invention air freshener candle product preferably is selected from the class of thermoplastic resins which in general are adapted for fiber-formation by processes such as extrusion or compression molding. It is preferred that the polymer is composed of elements which do not convert into noxious vapors under candle combustion conditions, such as carbon monoxide, hydrogen and oxygen.

Equipment and processes for polymer fiber-formation by extrusion are described in publications such as U.S. Pat. Nos. 3,065,502; 3,351,695; 3,577,588; 4,134,714; 4,302,409; and 5,320,798; incorporated by reference.

Suitable fiber-forming polymers include hydrocarbyl polyolefinic derivatives such as low and high density polyethylene, low and high density polypropylene, polybutene, polystyrene, and the like.

Other types of suitable polymers include polyvinyl acetate, polyvinyl alcohol/acetate, and acrylate resins such as polymethyl acrylate, polymethyl methacrylate, polybutyl methacrylate, poly(ethyl acrylate/ethylene), and the like.

Other preferred types of polymers include cellulosic derivatives such as cellulose acetate, methylcellulose, ethylcellulose, and the like.

Other types of polymers such as thermoset resins can be utilized by pressure molding a powder blend of candlewax, resin and air freshener-release cellulosic filler. Other components can be included in a candle composition such as stearic acid or particulate polysaccharidic filler which does not contain chemically-bound air freshener, such as starch or guar gum.

The air freshener-release cellulosic filler ingredient of an invention wick composition typically is in the form of a powder, or in the form of fine fibers which have an average length between about 0.3–3 centimeters.

The cellulosic substrate of the filler ingredient can be obtained from vegetable sources such as cotton, linen, flax, hemp, jute, wood pulp, and the like. The cellulosic substrate can be in the form of substituted derivatives such as cellulose acetate or methylcellulose, which additionally have a content of chemically-bound air freshener constituent.

The term "cellulosic" as employed herein refers to a β-glucosidic polysaccharide corresponding to the formula:

$[C_6H_7O_2(OH)_3]_n$ where n is an integer which provides an average molecular weight between about 100,000–2,000,000.

Formation of an invention air freshener candle product can be accomplished by the extrusion of a flaked or particulate blend of the candle ingredients, or by compression molding of the blended ingredients.

A unique aspect of the present invention is the provision of a cellulosic filler ingredient which has a content of chemically-bound air freshener constituent, and which releases the air freshener constituent into the atmosphere under the pyrolysis conditions of candle burning.

The term "chemically-bound" as employed herein refers to a covalent bond between a cellulose polymer chain and an air freshener molecule, such as an ether or ester linkage. The Degree of Substitution (D.S.) can be between about 0.05–3.

The term "air-freshener" as employed herein is meant to include fragrances such as geraniol, insect repellants such as citronellal, and therapeutic agents such as menthol.

An air freshener constituent of a present invention candle product can be any inherently volatile organic compound which is capable of being covalently linked to a cellulosic substrate by chemical reaction.

Suitable volatile air freshener compounds include alcohols such as undecanol, 4-isopropyl-cyclohexanol, geraniol, linalool, citronellol, farnesol, menthol, 3-trans-isocamphylcyclohexanol, benzyl alcohol, 2-phenylethyl alcohol, 3-phenyl-propanol, 3-methyl-5-phenylpentanol, cinnamic alcohol, isoborneol, thymol, eugenol, isoeugenol, anise alcohol, methyl salicylate, and the like.

Other suitable air freshener compounds include aldehydes and ketones such as hexanal, decanal, 2-methyldecanal, trans-2-hexenal, acetoin, diacetyl, geranial, citronellal, methoxydihydro-citronellal, menthone, carvone, camphor, fenchone, ionone, irone, damascone, cedryl methyl ketone, muscone, civetone, 2,4-dimethyl-3-cyclohexene carboxaldehyde, 2-heptylcyclopentanone, cis-jasmone, dihydrojasmone, cyclopentadecanone, benzaldehyde, phenylacetaldehyde, dihydrocinnamaldehyde, cinnamaldehyde, α-amylcinnamaldehyde, acetophenone, benzylacetone, benzophenone, piperonal, and the like.

Other suitable air freshener compounds include esters such as trans-2-hexenyl acetate, allyl 3-cyclohexylpropionate, methyl cinnamate, benzyl cinnamate, phenylethyl cinnamate, and the like.

The chemical-bonding of an alcohol air freshener such as geraniol or menthol to a cellulose polymer can be accomplished by the formation of a carbonate ester linkage:

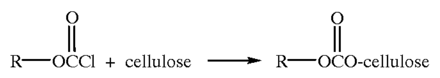

The reaction proceeds readily in the presence of a basic reagent such as sodium hydroxide or an organic amine. The production of cellulose carbonates are described in publications such as U.S. Pat. No. 3,705,890 and U.S. Pat. No. 5,068,321; incorporated by reference.

Another chemical means for forming a linkage between an alcohol air freshener and a cellulose polymer is by the use of an alcohol epichlorohydrin derivative under alkaline reaction conditions.

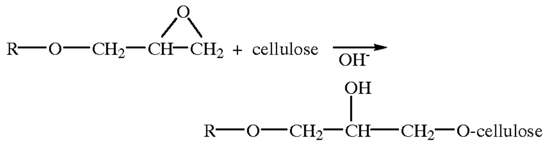

The chemical-bonding of an aldehyde such as citronellal or a ketone such as fenchone to a cellulose polymer can be accomplished by the formation of a hemiacetal (ketal) and/or acetal (ketal) linkage under acidic conditions:

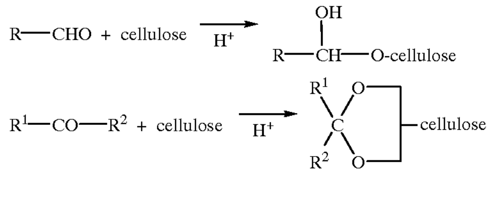

The chemical bonding of an ester such as phenylethyl cinnamate air freshener to a cellulose polymer can be accomplished by a Michael addition reaction under alkaline conditions:

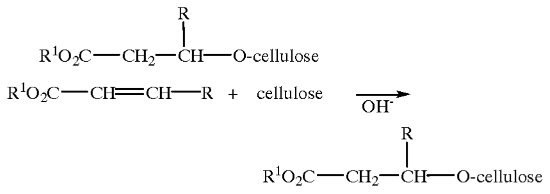

The Michael addition reaction is described in publications such as U.S. Pat. No. 2,415,040 and U.S. Pat. No. 5,569,779; incorporated by reference.

The chemical-bonding of an air freshener constituent to a saccaridic molecule in a cellulosic filler ingredient of a present invention candle composition provides significant advantages not previously contemplated by the prior art.

The air freshener constituent is released only when the candle product is being combusted. The air freshener is released by pyrolysis at a sustained constant rate.

The amount of air freshener constituent which is chemically-bound in the cellulosic substrate can be predetermined within a D.S. range between about 0.05–3 by selected synthesis conditions.

Because the air freshener constituent is chemically bound, there is no premature loss of air freshener by migration and evaporation.

A present invention air freshener candle product provides other desirable advantages. An invention candle product is wickless, and can be produced economically by a continuous extrusion process. A preferred invention candle product burns with a clean bright flame, and there is little or no wax dripping or residual ash formation.

A present invention air freshener candle product also can be extruded into a flexible taper filament which can be spiral wound for incorporation in an air freshener dispensing device.

The following examples are further illustrative of the present invention. The components and specific ingredients are presented as being typical, and various modifications can be derived in view of the foregoing disclosure within the scope of the invention.

EXAMPLE I

This Example illustrates the preparation of geraniol glycidyl ether.

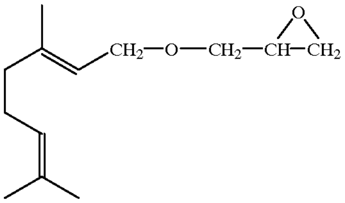

Geraniol (100 g) is added dropwise to a stirred mixture of 50% aqueous sodium hydroxide (300 mL), epichlorohydrin (300 g), and tetrabutylammonium hydrogen sulfate (60 g) with cooling to maintain a temperature of 20° C.

After a reaction period of 18 hours, the mixture is poured into water (one liter), and the aqueous medium is extracted with chloroform. The extract layer is washed with water, dried over sodium sulfate and filtered, and an oil product is recovered after solvent evaporation. NMR and IR confirm the structure.

EXAMPLE II

This Example illustrates the preparation of an air freshener candle product having a content of air freshener-release filler in accordance with the present invention.

A reactor equipped with a reflux condenser and stirrer is charged with hexane (one liter), caustic solution (20 g of 50% aqueous sodium hydroxide), and cellulose fibers (30 g; 0.5 cm average length). The mixture is stirred for 30 minutes at 25° C. under a nitrogen atmosphere.

Geraniol glycidyl ether (50 g) is added to the slurry, and the resulting reaction mixture is heated at 75° C. for 10 hours. The mixture then is cooled to room temperature, neutralized with glacial acetic acid, and filtered.

The recovered cellulose fibers are washed with acetone and then with water. After drying, solid state NMR indicates that the cellulosic matrix has a D.S. of 0.35.

Paraffin wax (MP 55° C.; 65 parts), polyethylene powder (MP 120° C.; 20 parts) and the above-described geraniol-substituted cellulosic filler (15 parts) are blended. The blend is passed through an extruder under heat and pressure to form a rigid circular-shaped candle matrix (0.6 cm diameter).

A cut section of the continuous extrusion candle product is ignited, and a flame persists until the candle is completely consumed. The combustion releases a flowery rose aroma which is characteristic of geraniol.

EXAMPLE III

This Example illustrates the preparation of an air freshener candle product having a content of fragrance-release cellulosic filler in accordance with the present invention.

Following the general procedure of Example I, glycidyl ethers are formed with the constituents of a perfume oil:

| | Parts |
|---|---|
| hydroxycitronellal | 18.0 |
| cinnamyl alcohol | 1.7 |
| terpineol | 8.0 |
| benzyl alcohol | 18.0 |
| phenethyl alcohol | 20.0 |
| linalool | 2.0 |

In a manner similar to that described in Example II, a slurry of cellulose powder is treated with the glycidyl ether mixture to chemically-bind the fragrance constituents to the cellulosic matrix (a D.S. of 0.6).

Beeswax (MP 66° C.; 78 parts) polystyrene powder (MP 115° C.; 15 parts) and the above-described fragrance-release cellulosic filler (7 parts) are blended. The blend is passed through an extruder under heat and pressure to form a rigid square-shaped candle matrix (0.3×0.3 cm).

A cut section of the continuous extrusion candle product is ignited, and a flame persists until the candle is completely consumed. The combustion releases a flowery lilac note into the atmosphere.

A similar result is obtained when the polymer ingredient is cellulose acetate or polyvinyl alcohol/acetate.

EXAMPLE IV

This Example illustrates the preparation of menthyl chloroformate.

A reactor in a dry-ice/acetone bath (−75° C.) is charged with liquid phosgene (117 g). Menthol (130 g), dissolved in 500 mL of cyclopentane, is added dropwise to the phosgene with stirring. The reaction medium is refluxed for six hours at room temperature.

The excess phosgene and cyclopentane are removed under reduced pressure. The recovered menthyl chloroformate is dissolved in diethyl ether (300 mL), and the solution is washed with aqueous sodium bicarbonate, and then with distilled water. The liquid medium is dried over sodium sulfate, and the solvent is removed under reduced pressure to yield a purified menthyl chloroformate.

EXAMPLE V

This Example illustrates the preparation of an air freshener product having a content of menthol-release cellulosic filler in accordance with the present invention.

Cellulose powder (400 g) is suspended in a blend of pyridine (1800 g) and benzene (3 liters), and the admixture is stirred for 20 hours at room temperature.

A 1200 g quantity of menthyl chloroformate is added dropwise to the stirred reaction medium at room temperature. The stirring is continued for 12 hours at a reaction medium temperature of 85° C. After cooling and filtering, the recovered cellulose powder is washed with benzene, then with isopropanol and with water. The wick product has a menthyl carbonate D.S. of 1.1.

Paraffin wax/10% microcrystalline wax (MP 68°–71° C.; 55 parts), polypropylene powder (MP 110° C.; 25 parts) and the above-described menthol-release cellulosic filler (20 parts) are blended. The blend is passed through an extruder under heat and pressure to form a rigid oval-shaped candle matrix (1.4×0.5 cm).

A cut section of the continuous extrusion candle product is consumed completely when ignited. A distinct aroma of menthol is detectable in the atmosphere during the candle burning.

EXAMPLE VI

This Example illustrates the preparation of an air freshener candle product having a content of citronellal-release cellulosic filler in accordance with the present invention.

A reactor is equipped with a stirrer and a reflux condenser having a water-removal unit. The reactor is charged with benzene (500 mL), p-toluenesulfonic acid (50 mg), citronellal (50 g) and cellulose powder (30 g).

The admixture is heated at reflux with stirring, and continued until no more water is entrained as an azeotrope. After cooling, the acid catalyst is neutralized with ammonium hydroxide. The mixture is filtered, and the recovered cellulose powder is washed with water. After drying, solid state NMR indicates that the cellulosic matrix has a D.S. of about 0.2.

Montan wax (MP 81–85° C.; 82 parts), polyethylene powder (MP 128° C.; 14 parts) and the above-described citronellal-release cellulosic filler (4 parts) are blended. The blend is passed through an extruder under heat and pressure to form a semi-rigid circular-shaped candle matrix (0.4 cm diameter).

A cut section of the continuous extrusion candle product is ignited, and it burns cleanly without residual ash formation. A citronellal aroma is released during the candle burning.

What is claimed is:

1. An air freshener candle product which is a taper-shaped combustible body comprising:

(a) between about 45–85 weight percent of candle wax ingredient;

(b) between about 10–35 weight percent of thermoplastic polymer ingredient; and (c) between about 0.1–20 weight percent of particulate cellulosic filler ingredient having air freshener chemically bound to the cellulosic filler;

wherein the air freshener constituent is released into the atmosphere under candle burning conditions.

2. A candle product in accordance with claim 1 which is produced by a continuous molding process.

3. A candle product in accordance with claim 1 wherein the taper-shaped combustible body is a cylindrical structure having a diameter between about 0.3–1.5 centimeters.

4. A candle product in accordance with claim 1 wherein the polymer ingredient comprises a polyolefinic resin.

5. A candle product in accordance with claim 1 wherein the polymer ingredient is selected from the group consisting of polyethylene, polypropylene, polystyrene and polyvinyl acetate.

6. A candle product in accordance with claim 1 wherein the polymer ingredient comprises a cellulose derivative.

7. A candle product in accordance with claim 1 wherein the polymer ingredient comprises cellulose acetate.

8. A candle product in accordance with claim 1 wherein the degree of air freshener substitution (D.S.) in the cellulosic filler ingredient is between about 0.05–3.

9. A candle product in accordance with claim 1 wherein the air freshener constituent is chemically-bound by an ether linkage within the cellulosic filler ingredient.

10. A candle product in accordance with claim 1 wherein the air freshener constituent is chemically-bound by an ester linkage within the cellulosic filler ingredient.

11. A candle product in accordance with claim 1 wherein the air freshener constituent after release as a reconstituted alcohol group.

12. A candle product in accordance with claim 1 wherein the air freshener constituent after release has a reconstituted carbonyl group.

13. A candle product in accordance with claim 1 wherein the air freshener constituent after release has a reconstituted olefin group.

14. A candle product in accordance with claim 1 wherein the air freshener constituent after release is a fragrance composition.

15. A candle product in accordance with claim 1 wherein the air freshener constituent after release is an insect repellant composition.

16. A candle product in accordance with claim 1 wherein the air freshener constituent after release is a therapeutic composition.

17. A candle product in accordance with claim 1 wherein the released air freshener comprises geraniol.

18. A candle product in accordance with claim 1 wherein the released air freshener comprises citronellal.

19. A candle product in accordance with claim 1 wherein the released air freshener comprises menthol.

20. A candle product in accordance with claim 1 which is a flexible taper filament that is adapted for spiral winding.

* * * * *

UNITED STATES PATENT AND TRADEMARK OFFICE

CERTIFICATE OF CORRECTION

PATENT NO. : 6,036,925

DATED : March 14, 2000

INVENTOR(S) : Mary Beth Adams et al.

It is certified that error appears in the above-identified patent and that said Letters Patent is hereby corrected as shown below:

<u>Column 4,</u>

```
                                                    R
                                                    |
Line 26, delete the first occurrence of [R1O2C-CH2-CH-O-celloulose].
```

<u>Claim 11,</u>

Line 2, replace [as] with <u>has.</u>

Signed and Sealed this

Twentieth Day of November, 2001

*Attest:*

NICHOLAS P. GODICI

*Attesting Officer*

*Acting Director of the United States Patent and Trademark Office*